(12) United States Patent
Ewing et al.

(10) Patent No.: US 6,398,713 B1
(45) Date of Patent: Jun. 4, 2002

(54) MAGNETIC THERAPEUTIC DEVICE

(76) Inventors: David L. Ewing, 15340 Bealfred, Fenton, MI (US) 48430; Randy G. Johnson, 6415 Fetterbush La., Bradenton, FL (US) 34202

(*) Notice: Subject to any disclaimer, the term of this patent is extended or adjusted under 35 U.S.C. 154(b) by 0 days.

(21) Appl. No.: 09/590,969

(22) Filed: Jun. 9, 2000

Related U.S. Application Data

(60) Provisional application No. 60/138,726, filed on Jun. 11, 1999.

(51) Int. Cl.[7] .............................. A61B 17/52; A61N 2/00
(52) U.S. Cl. ................................................... 600/9
(58) Field of Search .......................... 600/9, 15; 2/425; 433/18

(56) References Cited

U.S. PATENT DOCUMENTS

| | | | | |
|---|---|---|---|---|
| 4,511,330 A | * | 4/1985 | Smiley et al. | 433/18 |
| 5,228,143 A | * | 7/1993 | Marchello | 2/425 |
| 5,720,046 A | * | 2/1998 | Lopez et al. | 600/15 |

FOREIGN PATENT DOCUMENTS

| | | | | |
|---|---|---|---|---|
| JP | 405245218 A | * | 9/1993 | 600/9 |
| JP | 405317354 A | * | 12/1993 | |

* cited by examiner

*Primary Examiner*—Kevin Shaver
*Assistant Examiner*—Brian Szmal
(74) *Attorney, Agent, or Firm*—Dean Watson

(57) ABSTRACT

A magnetic therapeutic device having a magnetic source and a body for inserting into a human cavity, the body supporting the magnetic source in a position to deliver therapeutic effects to the body. Also described herein is a magnetic therapeutic device having a body with a magnetic source supported in a position for delivering a magnetic field to the temporal/mandibular region of a human head.

16 Claims, 3 Drawing Sheets

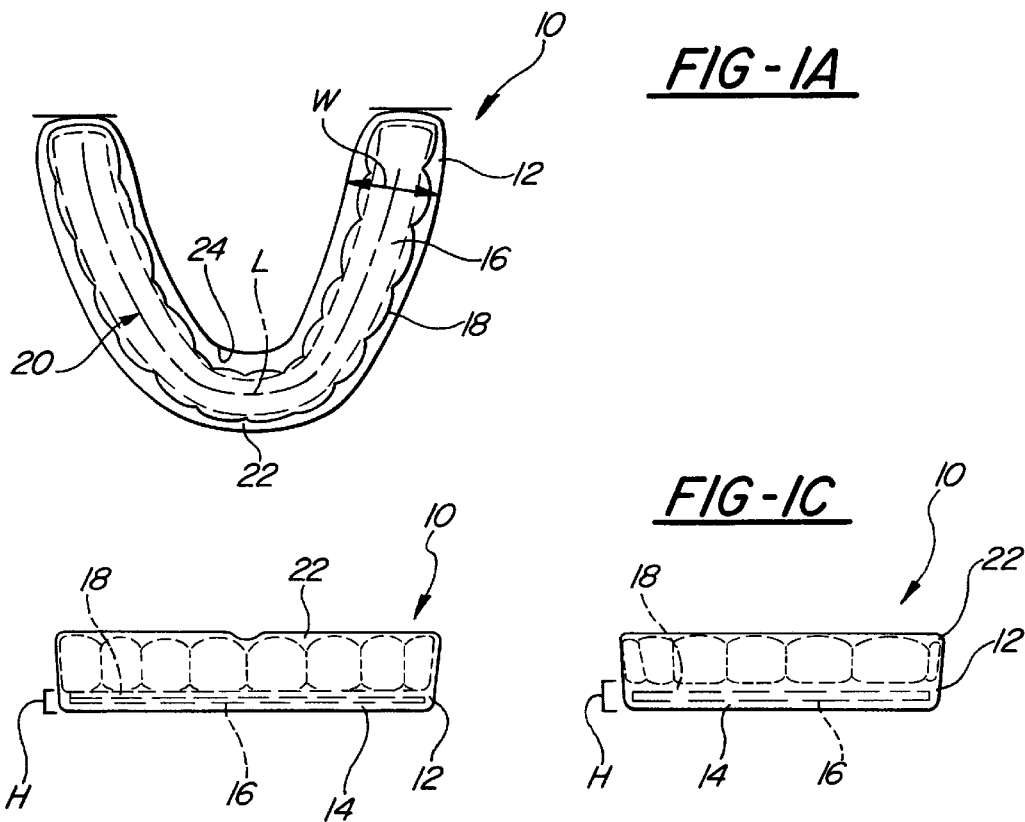
FIG-1A
FIG-1B
FIG-1C
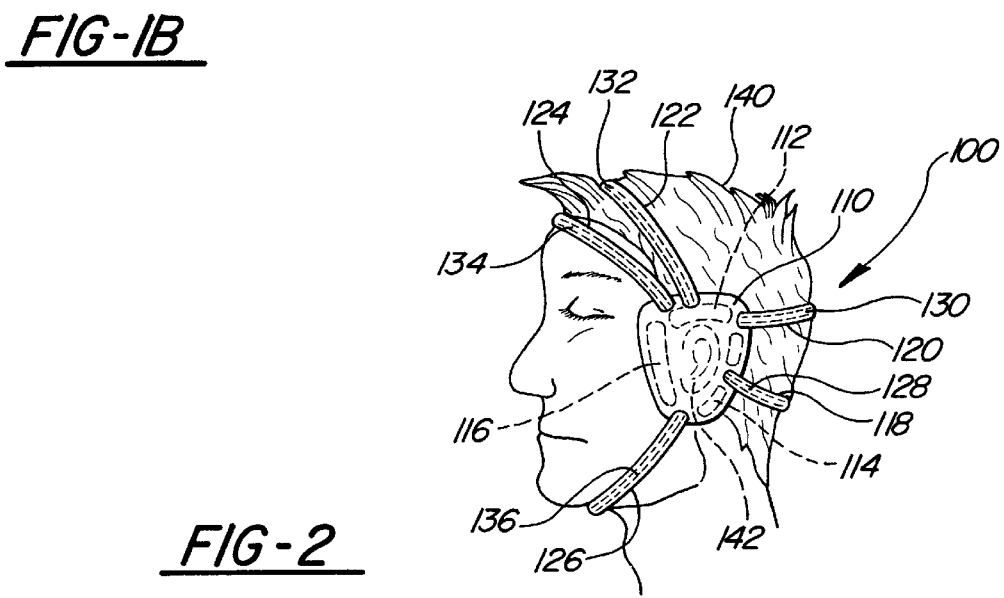
FIG-2

MAGNETIC THERAPEUTIC DEVICE

REFERENCE TO RELATED APPLICATIONS

The present invention is a completion of co-pending U.S. Provisional Patent Application S.N. 60/138,726, entitled "Magnetic Theraputic Device", filed Jun. 11, 1999, the disclosure of which is hereby incorporated by reference.

BACKGROUND OF THE INVENTION

1. Field of the Invention

The present invention pertains to magnetic therapeutic devices. More particularly, the present invention pertains to devices for the application of magnetic fields to specific regions of the human body.

2. Description of the Background Art

Magnets or biomagnets have long been used to expose particular regions of the human body to magnetic flux lines. The influence of biomagnets has been reported to improve circulation and reduce inflammation. As a result, pain may be reduced and strength may be increased.

A number of flexible magnetic pads have been disclosed to the public as providing therapeutic effects, including those disclosed in U.S. Pat. Nos. 5,514,072 and 5,538,495 (a flexible magnetic pad with multi-directional constantly alternating polarity zones); U.S. Pat. No. 5,549,532 (a flexible magnetic sheet for therapeutic use); and U.S. Pat. No. 5,304,111 (a therapeutic magnetic sheet with repeated curved areas); the disclosures of which are herein incorporated by reference. The magnetic pads are applied to various regions of the body, such as the legs and arms.

Additionally, magnets have been placed in wraps, jewelry and the soles of shoes to provide therapeutic effects. Magnets have also been incorporated into numerous other devices, such as those described in U.S. Pat. No. 4,480,596 (lumbar belts), U.S. Pat. No. 5,642,739 (armbands), and U.S. Pat. No. 5,720,046 (clothing). Each device is used for exposing a specifically defined, external regions of the human body to a magnetic field.

It has been reported that biomagnets can be placed at strategic points on the body to positively influence pain control by directing magnetic fields to acupuncture points, acupuncture meridians, and the surrounding hard and soft tissue. For example, clothing having discrete magnets attached thereto for producing healing effects at acupuncture points has been disclosed in U.S. Pat. No. 5,720,046, which issued Feb. 24, 1998 to Lopez et al., the disclosure of which is herein incorporated by reference. More specifically, Lopez teaches clothing and other personal wear which utilizes discrete magnets to direct magnetic fields towards acupuncture points along the human torso; acupuncture points on the head along the temporal region, soft spot and upper most vertebrae region at the base of the skull; and acupuncture points on the body appendages.

Although magnetic fields have been applied to a number of locations along the outer human body, none of the above cited patents teach or suggest the use of magnets for primarily applying a magnetic field to the lower temporal/mandibular region of a human head. Further none of the above cited patents teach or suggest inserting magnetic devices into cavities of the human body.

The lower temporal/mandibular region, as defined throughout this disclosure, refers to particular skeletal regions of the face and cranium along with the surrounding soft tissue. More specifically, the lower temporal/mandibular region includes the zygomatic bone, mandible, lower portion of the temporal bone, mastoid process, zygomatic arch, maxillae and surrounding soft tissue. The region of exposure preferably includes that region which is proximate the joint connecting the jaw to the cranium, longitudinally extending from the top of the ears to the tip of the chin and latitudinally extending the width of the lower portion of the jaw bone to the upper portion of the cheek bone. Additionally, none of the patents referred to above have disclosed or suggested the application of magnetic fields to the outer ear, the middle ear or the inner ear, the inside of the mouth or mouth cavity or to a healing wound. It is believed that application of a magnetic field to the lower temporal/mandibular region of the human head or within certain body cavities will positively impact blood circulation and cell polarity, thus reducing pain, fatigue, and stress, thereby increasing strength.

SUMMARY OF THE INVENTION

The present invention, to address the above stated deficiency in the background art devices as well as others, as is detailed hereinafter, provides means for delivering a magnetic field to the lower temporal/mandibular region of a human head. The present invention also provides a device having a magnetic source for inserting into a body cavity.

In a first embodiment, the present invention provides a mouthpiece comprising a magnetic device or magnet disposed therein.

In a second embodiment, the present invention provides headgear having means for positioning a magnetic device or magnet about the lower temporal/mandibular region of a human head and at least one magnetic device or magnet disposed within the means for positioning.

In a third embodiment, the present invention comprises an earplug having at least one magnetic device or magnet disposed therein.

In a fourth embodiment, the present invention provides a container or bottle for producing magnetic water, the container comprising at least one magnetic device circumferentially disposed about the container to magnetically charge water. The magnetic water being suitable for applying to a human body.

In a fifth embodiment of the present invention, the present invention provides magnetic dental or medical cement, the magnetic dental or medical cement comprising from about 1% to about 99.0% by total weight of magnetic water.

In a sixth embodiment, the present invention comprises a removable adhesive bandage having at least one magnetic device disposed therein.

For a more complete understanding of the present invention, reference is now made to the following detailed description and accompanying drawings.

BRIEF DESCRIPTION OF THE DRAWINGS

FIG. 1a is a top view of a first embodiment of a magnetic therapeutic device in accordance with the present invention;

FIG. 1b is a front view of a first embodiment of a magnetic therapeutic device in accordance with the present invention;

FIG. 1c is a side view of a first embodiment of a magnetic therapeutic device in accordance with the present invention;

FIG. 2 is an environmental view of a second embodiment of a magnetic therapeutic device in accordance with the present invention;

DETAILED DESCRIPTION

Figure 3A:
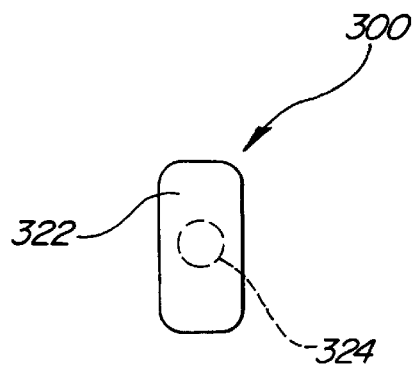
FIG. 3a is a side view of a third embodiment of a magnetic therapeutic device in accordance with the present invention.

With more particularity and with reference to FIGS. 1a–1c there is depicted therein a magnetic therapeutic device in accordance with the present invention comprising a mouthpiece, which is generally denoted at 10. The mouthpiece 10 comprises a bite plate 12 and at least one magnetic device 16 disposed therein. In addition to providing magnetic therapeutic effects to the maxillo-facial regions, the mouthpiece may additionally protect the oral infrastructure and favorably alter the vertical height of the dental occlusion to positively influence pain control and enhance strength and endurance.

The bite plate 12 has a height H, width W, and length L adapted to fit within the mouth of either an adult or child. The bite plate 12 separates the upper teeth from the lower teeth by the height H of the bite plate 12. Preferably, the height or separation H of the bite plate 12 provides from about 2 mm to about 3 mm of clearance between the posterior molars and from about 6 mm to about 8 mm of clearance between the anterior incisors. The bite plate 12 may be U-shaped or parabolic so as to properly fit about the teeth. The length L of the bite plate 12 preferably extends along the entire length of the bottom and the top rows of teeth. The bite plate 12 may comprise a plurality of peaks and valleys (not shown) that conform to or fit about the individual teeth of a human mouth.

The bite plate 12 may be a conventional mouth guard, bite splint or the like. Suitable mouth guards, in addition to others, include those disclosed in U.S. Pat. No. 4,791,941, which issued on Dec. 20, 1988 to Quinton, and U.S. Pat. Nos. 3,250,272, 3,211,143, 2,630,117, 3,224,441, 3,124,129, 3,096,761, 3,112,744, the disclosures, all of which, are herein incorporated by reference.

The bite plate 12 may further have at least one channel 20 for seating the teeth of the human mouth therein. The bite plate 12 may have at least one wall 22, and preferably a second wall 24. extending therefrom to form the channel 20. The channel 20 may be preformed within the bite plate to conform to either the teeth or the gums of a human mouth or both, as may be the case for a person who does not have teeth. The channel 20 may house either the upper set of teeth, the lower set of teeth, or may house both or the upper gums, the lower gums or both. Preferably, the channel 20 fits about the upper set of teeth. The channel 20 is adapted to hold the mouthpiece 10 securely in place and may additionally protect the teeth from a frontal blow to the mouth.

The channel 20 may be preformed or custom fit to a particular individual's mouth and bite pattern. For example, a cast of the teeth or gums may be taken to form a die-cast of the mouthpiece 10 of hard plastic.

The bite plate 12 may be formed of semi-ridged rubber or plastic, pliable rubber, rigid plastic, or like materials. Pliable rubber or pliable plastic allows the bite plate 12 to be used as an athletic mouth guard. The favorable protective mechanism provided by a semi-ridged material between the maxillary and mandibular detention will help prevent tooth trauma, oral lacerations, temporal/mandibular joint dysfunction, and cranial/sacral injury. The bite plate 12 may also be substantially formed of thermoplastic. Thermoplastic allows an end user to heat the bite plate in hot water and mold the bite plate to the end user's specific bite profile.

Alternatively, the bite plate 12 may be formed of a hard plastic or rubber. Hard rubber or plastic allows the bite plate 12 to be used as a bite splint. A bite splint reduces wear between the upper teeth and lower teeth and may be used by people who grind their teeth.

It is critical to the present invention that the mouthpiece 10 have a magnetic source, magnetic device or magnet 16 disposed therein. As shown, the magnetic 16 resides between a bottom layer 14 and a top layer 18 of the bite plate 12. The bottom layer 14, the magnetic device 16, and the top layer 18 preferably provide a separation H of about 2 mm to about 10 mm between the top set of teeth and the bottom set of teeth. Alternatively, the magnetic device may be made integral (not shown) with the bite plate to form a single, uniformly and integrally constructed magnetic mouthpiece, such as a soft material or body having magnetic properties.

The magnetic device 16 is disposed within the bite plate 12 using any suitable means of manufacture including molding the bite plate around the magnetic device, layering the bite plate between the bottom layer and top layer and securing the magnetic device with adhesives, etc. Alternatively, as in the case where the magnetic device is made integral with the bite plate (not shown), the manufacture of such device may be accomplished by embedding magnetic ferrite particulates within a semi-rigid plastic or rubber bite plate and forming the bite plate to fit about the teeth.

The magnetic device 16, and those described throughout the ensuing disclosure, may be anything that produces a magnetic field, including for example a discrete ferrite magnet, a plurality of discrete ferrite magnets, an electromagnet, etc. Preferably, the magnetic device 16 is a rubbery-flexible synthetic material in which permanent magnetic ferrite particles have been imbedded. The magnetic device generates a magnetic flux density of about 50 to about 2500 gauss. The magnetic device preferably has a magnetic flux density of about 400 to about 1000 gauss and more preferably from about 800 to about 1000 gauss.

The magnetic device 16 may comprise constantly alternating north/south polarity zones. The magnetic device may also comprise a flexible planar magnetic sheet having a specific pattern of repeating alternating polarity, such that poles of the same polarity are disposed about the magnetic device 16 in a staggered position. The magnetic device 16 may be formed of a flexible magnetic sheet having a variety of patterns including: a spiral pattern emanating from the center of the device and having magnetic poles of alternating polarity, or some other geometric shape, such as concentrically arranged rings, sectors, quadrangles or the like.

The magnetic source is disposed in the mouthpiece 10 in an orientation suitable for exposing the joints, bones, and surrounding soft tissue to a magnetic field. In particular, when a flat magnetic device is used, the magnetic field radiating therefrom exposes the body tissue to a field flux at an angle of from about 45 to 90 degrees, relative to an axis formed by the surface of the flat magnetic device. Preferably, the magnetic device 16 is disposed within the bite plate 12 to deliver a magnetic field with a flux of about 90 degrees relative to the surface of the magnet to provide the maximum exposure of body tissue to the flux lines of the magnetic device.

Referring now to FIG. 2, shown therein is a magnetic therapeutic device in accordance with the present invention comprising headgear, shown generally at 100. The headgear comprises means 142 for positioning a magnetic device about an ear or about the lower temporal/mandibular region of the human head or both, wherein the means 142 for positioning has at least one magnetic device 116 disposed therein. The means 142 for positioning may be an ear guard, a support ring that encircles the ear, an ear covering, an earmuff, etc. As shown, the means for positioning the magnetic device comprises at least one ear guard 110 having at least one magnetic device 116 disposed within the ear guard 110. As may become evident from this disclosure, the headgear may further comprise two individual ear guards (not shown).

The ear guard 110 is adapted to shelter and protect the human ear. The ear guard 110 is preferably a convex housing having a thickness, an inner side and an outer side. The ear guard 110 may comprise a convex, hard shell or pliable covering. The hard shell may be formed of leather, plastic, rubber, etc. Padding may be attached to the inside of the hard shell using suitable fastening means, such as riveting, gluing, etc. Alternatively, the ear guard 110 may be comprised of a pliable covering without a hard outer shell. The pliable covering may be formed of leather, plastic or the like and padded with material, such as foam rubber, cotton batting or the like. Padding is used to cushion and absorb the force of blows that may be delivered to the ear.

Thus, the ear guard 110 may perform a multitude of purposes besides solely supporting the magnetic device: such as protecting the ears from physical blows, protecting the ears from cold temperatures, etc. The headgear of the present invention may resemble the types of headgear used in wrestling, hockey, baseball, football, water polo, cycling, etc. For example, a football helmet has a padded inner lining, the inner lining has a recess which encircles the ears, thus forming an ear guard within the helmet.

The ear guard 110 comprises at least one magnetic device or magnet 114 disposed therein. The ear guard 110 may comprise a plurality of magnets 114, 116, 112. As shown, three magnets are disposed 114, 116, 112 radially about a central portion of the ear guard. The magnets are parabolic or curved in shape and partially encircle the outer area of the ear. Alternatively or additionally, a single concave magnet (not shown) may be disposed in the ear guard and adapted to fit over the entire ear of a wearer.

The magnets disposed in the ear guard 110 expose the lower temporal bone, sphenoid bone, zygomatic arch, mandible and surrounding soft tissues to magnetic flux lines. The magnetic device may also expose the outer ear, middle ear, and inner ear to magnetic flux lines.

The headgear 100 may comprise a plurality of support straps 118, 120, 122, 124, 126 for removably supporting the ear guard 110 about a suitable position on the human head 140. Such straps may include a lower back strap 118, a middle back strap 120, an upper middle strap 122, and an upper frontal strap 124. At least one strap 118, 120, 122, 124, 126 of the headgear 100 may be a chinstrap 126. The chinstrap 126 is adjustable and provides means for fixing the position of the ear guard about the head 140. The straps 118, 120, 122, 124, 126 may be connected to the ear guard 110 in any suitable manner, such as by using fasteners, snaps, adhesives, stitching, looping the straps through at least one aperture of the ear protective device, etc.

Each strap 118, 120, 122, 124, 126 of the headgear 126 may comprise at least one corresponding magnetic device or magnet 128, 130, 132, 134, 136 disposed therein. The magnetic device 128, 130, 132, 134, 136 is preferably a rectilinear, flat, flexible magnet or a plurality of flat flexible magnets (not shown) disposed within the straps.

Figure 3B:
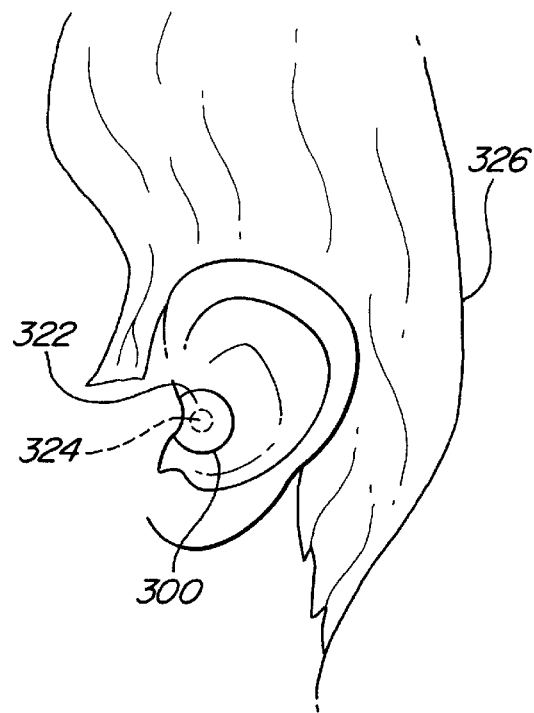
FIG. 3b is an environmental top view of a third embodiment of a magnetic therapeutic device in accordance with the present invention.

Now referring to FIGS. 3a and 3b, generally depicted therein is an earplug 300 comprising at least one magnetic device 324 disposed therein. A housing or plug portion 322 forms the outer structure of the earplug 300. The shape of the housing 322 is adapted for inserting the earplug 300 into the ear canal of the human head 326. Such shapes may include tubular, conical, rectangular with rounded edges, ovular, etc.

Additionally, the earplug 300 may be adapted to muffle sound. To muffle sound, the housing 322 is preferably formed of pliable rubber, foam plastic, or the like. The rubber or foam plastic acts to reduce sound waves entering through the ear canal.

The magnetic device 324 is disposed within the housing or support body 322 using suitable means, such as molding the housing 322 around the magnetic device, embedding and scattering magnetic ferrite particulates throughout the housing 322, etc. The housing 322 is formed to support the magnetic device 324 within the ear cannel and expose the outer ear, the middle ear, and the inner ear to the effects of the magnet. The middle ear includes the tympanic membrane, malleus, stapes, etc. The inner ear includes the cochlea, etc. It is believed that exposing these regions of the ear to the effects of magnetic fields, the magnetic fields will positively impact circulation and cell polarity to reduce pain and stress.

Figure 4:
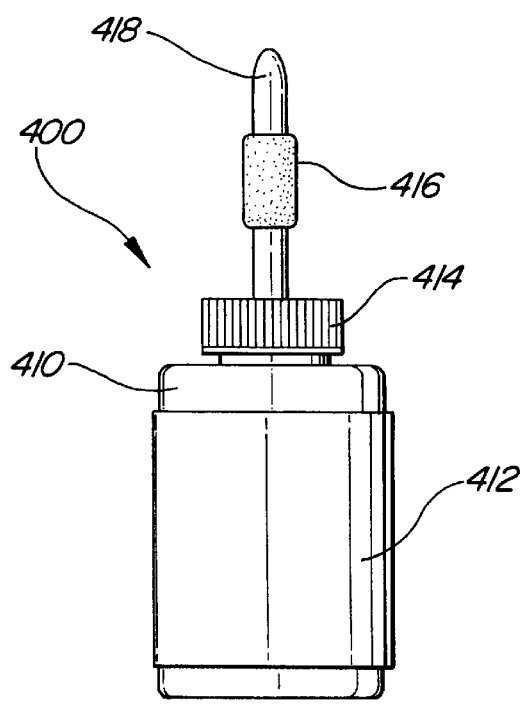
FIG. 4 is a side view of a fourth embodiment of a magnetic therapeutic device in accordance with the present invention.

Now referring to FIG. 4, generally depicted therein at 400 is a water bottle or container for producing magnetic water. The water bottle 400 comprises a housing 410 that forms a chamber for holding water and a magnetic device 412.

The magnetic device 412 may be disposed within the chamber, embedded in the walls of the housing 410, wrapped around the outside of the housing 410, etc. As shown, the magnetic device 412 is disposed about the housing 410 using suitable means. Suitable means include molding the housing around the magnetic device; embedding magnetic ferrite particulates throughout the housing; fixing a flexible flat magnetic around the outer walls of the housing with adhesives; etc. As shown, the water bottle 400 has at least one magnetic device 412 disposed around the outer circumference of the housing 410.

The magnetic device 412 is adapted for magnetizing water contained within the chamber. The magnetic device preferably produces a magnetic field having a field strength of about 400 to about 5,000 gauss. To magnetize water, water is placed in the bottle 400 and left to stand from about 1 minute to about 10 minutes. The water may be left to stand in the bottle for storage and ready use, the storage may last for hours, days, months, etc.

Additionally, the water bottle 400 may have a cap 414 for sealing the chamber. The water bottle 400 may further comprise an applicator tip 418 attached to the cap 414. The applicator tip may additionally have a second magnetic device 416 disposed about the applicator tip 418 for additionally magnetizing water that passes therethrough.

Magnetized water may be used in a number of applications, such as a mouthwash, in shampoo, in water-based plaster (such as medical casts), in toothpaste, in medical or dental cement, in dental bases and liners, and in desensitizing agents for providing magnetic therapeutic benefits.

Figure 5:
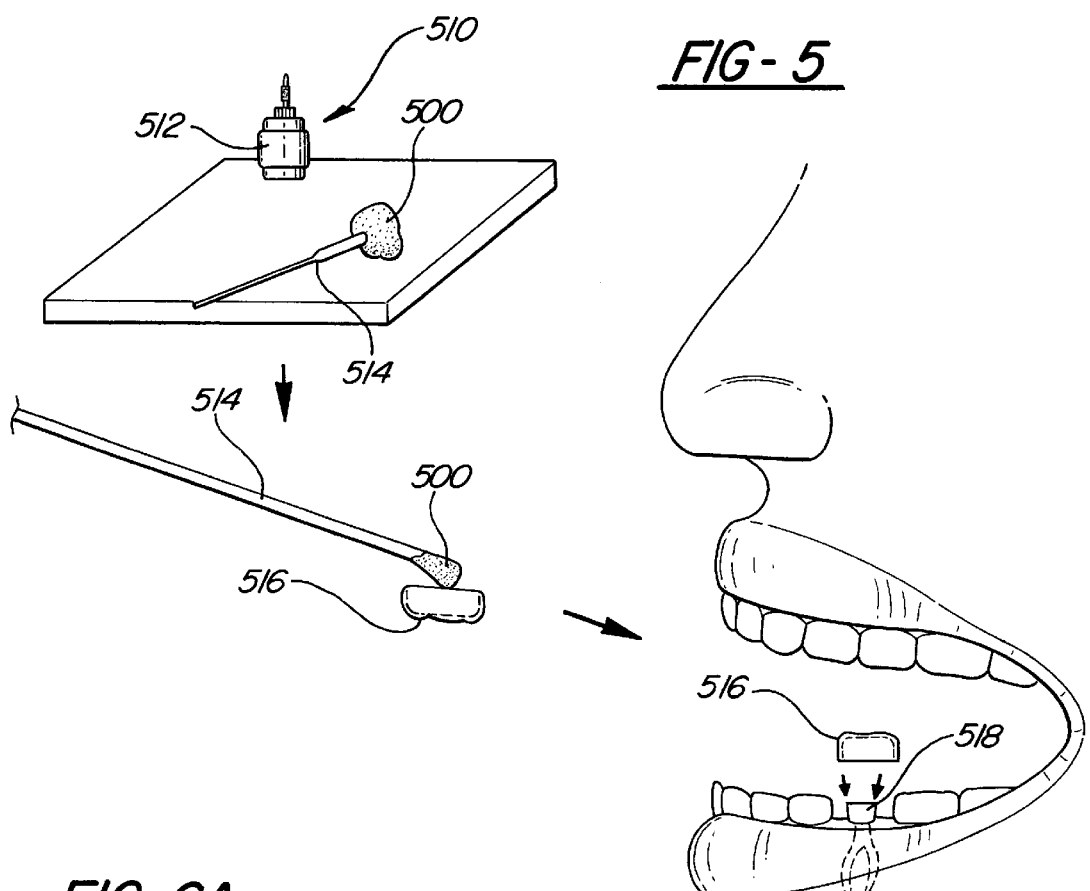
FIG. 5 is an environmental view of a fifth embodiment of a magnetic therapeutic device in accordance with the present invention.

Now referring to FIG. 5, shown therein and generally depicted at 500 is magnetized dental or medical cement. The magnetized dental cement 500 is used for attaching crowns, dental appliances, etc., within the human mouth. The magnetized dental cement 500 is produced by mixing magnetized water with a water-based dental cement. Magnetized or magnetic water is produced by adding water to a magnetizing water bottle 512 (such as the bottle disclosed above at 400). The water is left to stand in the magnetizing water bottle 512 for a suitable time, as described above, for magnetizing the water.

Magnetized water 510 from the magnetizing water bottle 512 is added to conventional powdered dental cement and stirred together using a suitable mixing apparatus 514. The magnetized water is stirred into the powered dental cement until the dental cement reaches a consistency such that the dental cement does not separate more than about 1 to 2 inches when drawn away form the mixing plate with the mixing apparatus.

Among others, conventional powdered dental cements include, for example, known water-based, carboxylate dental cements and those described in U.S. Pat. No. 5,154,762 and others, the disclosure of which is herein incorporated by reference.

The magnetic dental cement 500 is applied to the inside of a dental appliance 516 using a suitable apparatus 514. The dental appliance 516 is then fixedly attached to a prepared surface, such as a prepared tooth 518. The dental cement 500 having magnetic properties and applied to a tooth, exposes the tooth and the surrounding soft tissue to the effects of a magnetic field. The magnetic field positively impacts blood circulation and cell polarity to reduce pain and promote healing. Consequently, tooth comfort can be maintained and the surrounding periodontal structures will realize enhanced healing.

Figure 6A:
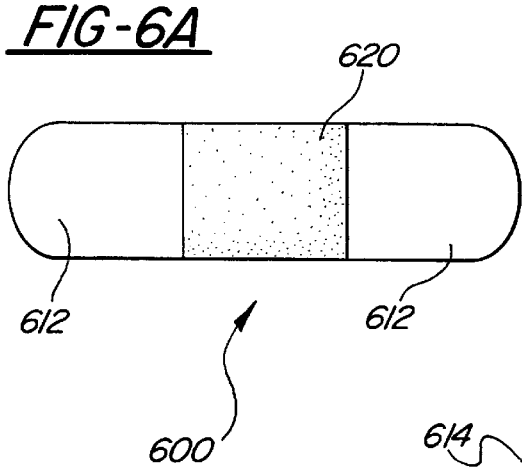
FIG. 6a is a bottom view of a sixth embodiment of a magnetic therapeutic device in accordance with the present invention.
Figure 6B:
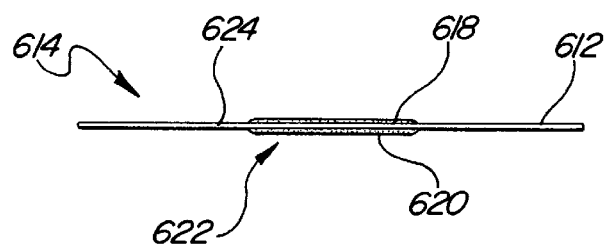
FIG. 6b is a cross-sectional side view of a sixth embodiment of a magnetic therapeutic device in accordance with the present invention.

Now referring to FIGS. 6a–6b, shown therein is an adhesive bandage, generally depicted at 600. The adhesive bandage 600 comprises a plastic strip 624, an absorbent material 620 attached to the plastic strip 624, an adhesive 612 disposed on the plastic strip 624, and at least one magnetic device or magnet 618 attached to the plastic strip 624.

The magnet 618 may be disposed about the adhesive bandage 600 in any location and held in place by suitable fastening means, such as adhesives, stitching, or the like. The magnet may also be removably attached to the adhesive bandage 600, such as by, for example, seating the magnet within a pocket (not shown) formed in the absorbent material.

As shown, the magnet 618 is located at a central portion of the adhesive bandage above a suitable adsorbent material 620. The magnetic device or magnet 618 preferably produces a magnetic field of from about 1 gauss to about 1000 gauss and more preferably from about 1 to about 50 gauss.

Suitable absorbent materials 620 used in the adhesive bandage include absorbent cotton, gauze or the like. Preferably, the absorbent material has a non-stick surface (not shown) for applying the absorbent material over a wound. Such non-stick material may be a mesh type material having tightly woven fibers that allow bodily fluids to pass therethrough without sticking the application spot.

The magnetic adhesive bandage 600 further comprises means 612 for attaching the bandage over a wound. The means 612 for attaching is, for example, a removable adhesive, tack or glue disposed upon a plastic strip 624.

In use, the magnetic adhesive bandage is applied over a wound with the adhesive portions of the plastic strip attached to healthy tissue and the magnet centered upon the damaged tissue. The magnetic adhesive bandage 600, by having at least one magnet disposed thereon, exposes the wound to the effects of a magnetic field to positively enhance circulation and cell polarity to thereby promote healing.

While the invention has been illustrated in detail in the drawings and in the foregoing description, the same is to be considered as illustrative and not restrictive in nature. It is understood that only the preferred embodiments have been shown and described fully and that all changes and modifications that come within the spirit of the invention are desired to be protected.

Thus, it is to be appreciated from the preceding disclosure that there has been described therein a magnetic therapeutic device for exposing the lower temporal/mandibular region of the human head to the effects of a magnetic field. It is also to be appreciated from the preceding specification that there has been described therein a magnetic therapeutic device having a body for inserting into a human cavity, the body having a magnetic source. It is also to be appreciated from the preceding specification that there has been described therein a magnetic therapeutic device, the magnetic therapeutic device comprising: a mouthpiece having at least one magnetic device disposed therein. It is also to be appreciated from the preceding specification that there has been described therein magnetic therapeutic headgear, the headgear comprising means for positioning a magnetic device about the ear or lower temporal/mandibular region of a human head and a magnetic device disposed within the means for positioning. It is also to be appreciated from the preceding specification that there has been described therein a magnetic therapeutic device, wherein the magnetic therapeutic device comprises an earplug having at least one magnetic device disposed therein. It is also to be appreciated from the preceding specification that there has been described therein a device for producing magnetic water, wherein the device comprises a water bottle having at least one magnetic device disposed about the circumference of the bottle. It is also to be appreciated from the preceding specification that there has been described therein a method of producing magnetic dental or medical cement. The magnetic dental or medical cement comprises water-based dental or medical cement having magnetic properties. It is also to be appreciated from the preceding specification that there has been described therein a magnetic therapeutic device wherein the device comprises a removable adhesive bandage having at least one magnet disposed therein.

What is claimed is:

1. A magnetic therapeutic device comprising:
   a mouthpiece having a bite plate, the bite plate being 2 mm to 10 mm in thickness; and
   a magnetic source disposed in the bite plate.

2. The magnetic therapeutic device of claim 1 wherein the magnetic source is a 50 to 2500 gauss, flexible, flat magnet which extends the length of the bite plate.

3. The magnetic therapeutic device of claim 2 wherein the magnetic source is a flexible, flat magnet.

4. The magnetic therapeutic device of claim 2 wherein the bite plate is adapted to provide about 2 mm to 3 mm of clearance between the posterior molars and about 6 mm to about 8 mm of clearance between the anterior incisors.

5. The magnetic therapeutic device of claim 4 wherein the magnetic source is adapted to provide 50 to 2500 gauss.

6. The magnetic therapeutic device of claim 5 wherein the magnetic source is 400 to 1000 gauss.

7. The magnetic therapeutic device of claim 5 wherein the magnetic source is 800 to 1000 gauss.

8. The magnetic therapeutic device of claim 4 wherein the bite plate is adapted to custom fit an individuals mouth.

9. The magnetic therapeutic device of claim 1 wherein the magnetic source is uniformly distributed throughout the bite plate.

10. The magnetic therapeutic device of claim 9 wherein the bite plate is adapted to custom fit an individuals mouth.

11. The magnetic therapeutic device of claim 9 wherein the bite plate is adapted to provide about 2 mm to 3 mm of clearance between the posterior molars and about 6 mm to about 8 mm of clearance between the anterior incisors.

12. The magnetic therapeutic device of claim 9 wherein the magnetic source is adapted to provide 50 to 2500 gauss.

13. The magnetic therapeutic device of claim 12 wherein the magnetic source is 400 to 1000 gauss.

14. The magnetic therapeutic device of claim 13 wherein the magnetic source is 800 to 1000 gauss.

15. The magnetic therapeutic device of claim 12 wherein the magnetic source is disposed within the bite plate to deliver a magnetic flux at about 45 to 90 degrees.

16. The magnetic therapeutic device of claim 15 wherein the magnetic flux is about 90 degrees.

* * * * *